US006988982B2

(12) United States Patent  
Melvin et al.

(10) Patent No.: US 6,988,982 B2  
(45) Date of Patent: Jan. 24, 2006

(54) HEART WALL ACTUATION SYSTEM FOR THE NATURAL HEART WITH SHAPE LIMITING ELEMENTS

(75) Inventors: David B. Melvin, Loveland, OH (US); Brad A. Klosterman, Nashville, TN (US); Alan J. Melvin, Cincinnati, OH (US)

(73) Assignees: Cardioenergetics, Cincinnati, OH (US); The University of Cincinnati, Cincinnati, OH (US)

(*) Notice: Subject to any disclaimer, the term of this patent is extended or adjusted under 35 U.S.C. 154(b) by 30 days.

(21) Appl. No.: 10/223,271

(22) Filed: Aug. 19, 2002

(65) Prior Publication Data

US 2004/0034271 A1 Feb. 19, 2004

(51) Int. Cl.  
*A61M 1/10* (2006.01)

(52) U.S. Cl. .......................... 600/16; 623/3.16
(58) Field of Classification Search ............. 600/16, 600/17, 37; 601/153; 623/3.1, 3.11, 3.17, 623/3.19, 3.22, 3.25

See application file for complete search history.

(56) References Cited

U.S. PATENT DOCUMENTS

| | | | |
|---|---|---|---|
| 2,826,193 A | 3/1958 | Vineberg | |
| 3,053,249 A | 9/1962 | Smith | |
| 3,455,298 A | 7/1969 | Anstadt | |
| 3,513,836 A | 5/1970 | Sausse | |
| 3,590,815 A | 7/1971 | Schiff | |
| 3,613,672 A | 10/1971 | Schiff | |
| 3,668,708 A | 6/1972 | Tindal | |
| 3,713,439 A | 1/1973 | Cabezudo | |
| 3,791,388 A | 2/1974 | Hunter et al. | |
| 3,827,426 A | 8/1974 | Paige et al. | |
| 3,983,863 A | 10/1976 | Janke et al. | |
| 4,192,293 A | 3/1980 | Asrican | |
| 4,536,893 A | 8/1985 | Parravicini | |
| 4,621,617 A | 11/1986 | Sharma | |

(Continued)

FOREIGN PATENT DOCUMENTS

| | | |
|---|---|---|
| WO | WO 00/18320 | 4/2000 |
| WO | WO01/67985 | 2/2001 |
| WO | WO 01/91667 | 12/2001 |

*Primary Examiner*—Robert E. Pezzuto  
*Assistant Examiner*—Frances P. Oropeza  
(74) *Attorney, Agent, or Firm*—Wood, Herron & Evans, LLP

(57) ABSTRACT

An actuation system for assisting the operation of the natural heart includes an actuator element adapted to be positioned proximate a portion of a heart wall. The actuator element is operable for acting on the heart wall portion to effect a change in the shape of the heart. A shape-limiting element is configured for being positioned proximate a heart wall. The shape-limiting element is operable for flexing to assume a curvature no greater than a predetermined curvature when the heart wall is acted upon and maintaining that predetermined curvature to control the shape of the actuated heart.

32 Claims, 7 Drawing Sheets

U.S. PATENT DOCUMENTS

| | | |
|---|---|---|
| 4,690,134 A | 9/1987 | Snyders |
| 4,809,676 A | 3/1989 | Freeman |
| 4,846,831 A | 7/1989 | Skillin |
| 4,904,255 A | 2/1990 | Chareire et al. |
| 4,936,857 A | 6/1990 | Kulik |
| 4,957,477 A | 9/1990 | Lundback |
| 5,109,843 A | 5/1992 | Melvin et al. |
| 5,119,804 A | 6/1992 | Anstadt |
| 5,131,905 A | 7/1992 | Grooters |
| 5,139,517 A | 8/1992 | Corral |
| 5,169,381 A | 12/1992 | Snyders |
| 5,192,314 A | 3/1993 | Daskalakis |
| 5,201,880 A | 4/1993 | Wright et al. |
| 5,256,132 A | 10/1993 | Snyders |
| 5,258,021 A | 11/1993 | Duran |
| 5,334,217 A | 8/1994 | Das |
| 5,345,949 A | 9/1994 | Shlain |
| 5,358,519 A | 10/1994 | Grandjean |
| 5,370,685 A | 12/1994 | Stevens |
| 5,383,840 A | 1/1995 | Heilman et al. |
| 5,385,528 A | 1/1995 | Wilk |
| 5,484,391 A | 1/1996 | Buckman, Jr. et al. |
| 5,487,760 A | 1/1996 | Villafana |
| 5,533,958 A | 7/1996 | Wilk |
| 5,571,176 A | 11/1996 | Taheri |
| 5,593,424 A | 1/1997 | Northrup, III |
| 5,655,548 A | 8/1997 | Nelson et al. |
| 5,702,343 A | 12/1997 | Alferness |
| 5,709,695 A | 1/1998 | Northrup, III |
| 5,713,954 A | 2/1998 | Rosenberg et al. |
| 5,738,626 A | 4/1998 | Jarvik |
| 5,738,627 A | 4/1998 | Kovacs et al. |
| 5,749,883 A | 5/1998 | Halpern |
| 5,800,528 A | 9/1998 | Lederman et al. |
| 5,824,071 A | 10/1998 | Nelson et al. |
| 5,910,124 A | 6/1999 | Rubin |
| 5,957,977 A * | 9/1999 | Melvin ..................... 623/3.1 |
| 5,961,440 A | 10/1999 | Schweich, Jr. et al. |
| 6,019,722 A | 2/2000 | Spence et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,077,214 A | 6/2000 | Mortier et al. |
| 6,085,754 A | 7/2000 | Alferness et al. |
| 6,110,100 A | 8/2000 | Talpade |
| 6,123,662 A | 9/2000 | Alferness et al. |
| 6,125,852 A | 10/2000 | Stevens et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,179,791 B1 | 1/2001 | Krueger |
| 6,183,411 B1 | 2/2001 | Mortier et al. |
| 6,214,047 B1 | 4/2001 | Melvin |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,293,906 B1 | 9/2001 | Vanden Hoek et al. |
| 6,319,231 B1 | 11/2001 | Andrulitis |
| 6,324,430 B1 | 11/2001 | Zarinetchi et al. |
| 6,324,431 B1 | 11/2001 | Zarinetchi et al. |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,375,611 B1 | 4/2002 | Voss et al. .................. 600/210 |
| 2001/0016675 A1 | 8/2001 | Mortier et al. |
| 2002/0007216 A1 * | 1/2002 | Melvin ..................... 623/3.11 |
| 2003/0023132 A1 | 1/2003 | Melvin et al. |

* cited by examiner

HEART WALL ACTUATION SYSTEM FOR THE NATURAL HEART WITH SHAPE LIMITING ELEMENTS

FIELD OF THE INVENTION

This invention relates generally to assisting the natural heart in operation by actuating a wall of the natural heart, and more specifically to facilitating such actuation without damage to the heart tissue.

BACKGROUND OF THE INVENTION

The natural human heart and accompanying circulatory system are critical components of the human body and systematically provide the needed nutrients and oxygen for operation of the body. As such, the proper operation of the circulatory system, and particularly, the proper operation of the heart, are critical in the life, health and well-being of a person. A physical ailment or condition which compromises the normal and healthy operation of the heart can therefore be particularly critical and may result in a condition which must be medically remedied.

More specifically, the natural heart, or rather the cardiac tissue of the heart, can degrade for various reasons to a point where the heart can no longer provide sufficient circulation of blood for maintaining the health of a patient at a desirable level. In fact, the heart may degrade to the point of failure and thereby may not even be able to sustain life. To address the problem of a failing natural heart, solutions are offered to provide ways in which circulation of blood might be maintained. Some solutions involve replacing the heart. Other solutions are directed to maintaining operation of the existing heart.

One such solution has been to replace the existing natural heart in a patient with an artificial heart or a ventricular assist device. In using artificial hearts and/or assist devices, a particular problem stems from the fact that the materials used for the interior lining of the chambers of an artificial heart are in direct contact with the circulating blood. Such contact may enhance undesirable clotting of the blood, may cause a build-up of calcium, or may otherwise inhibit the blood's normal function. As a result, thromboembolism and hemolysis may occur. Additionally, the lining of an artificial heart or a ventricular assist device can crack, which inhibits performance, even when the crack is at a microscopic level. Moreover, these devices must be powered by a power source which may be cumbersome and/or external to the body. Such drawbacks have limited the use of artificial heart and assist devices to applications having too brief of a time period to provide a real lasting health benefit to the patient.

An alternative procedure also involves replacement of the heart, but includes a transplant of a natural heart from another human or animal into the patient. The transplant procedure requires removing an existing organ (i.e. the natural heart) from the patient for substitution with another organ (i.e. another natural heart) from another human, or potentially, from an animal. Before replacing an existing organ with another, the substitute organ must be "matched" to the recipient, which can be, at best, difficult, time consuming, and expensive to accomplish. Furthermore, even if the transplanted organ matches the recipient, a risk exists that the recipient's body will still reject the transplanted organ and attack it as a foreign object. Moreover, the number of potential donor hearts is far less than the number of patients in need of a natural heart transplant. Although use of animal hearts would lessen the problem of having fewer donors than recipients, there is an enhanced concern with respect to the rejection of the animal heart.

Rather than replacing the patient's heart, other solutions attempt to continue to use the existing heart and associated tissue. In one such solution, attempts have been made to wrap skeletal muscle tissue around the natural heart to use as an auxiliary contraction mechanism so that the heart may pump. As currently used, skeletal muscle cannot alone typically provide sufficient and sustained pumping power for maintaining circulation of blood through the circulatory system of the body. This is especially true for those patients with severe heart failure.

Another system developed for use with an existing heart for sustaining the circulatory function and pumping action of the heart, is an external bypass system, such as a cardiopulmonary (heart-lung) machine. Typically, bypass systems of this type are complex and large, and, as such, are limited to short term use, such as in an operating room during surgery, or when maintaining the circulation of a patient while awaiting receipt of a transplant heart. The size and complexity effectively prohibit use of bypass systems as a long term solution, as they are rarely portable devices. Furthermore, long term use of a heart-lung machine can damage the blood cells and blood borne products, resulting in post surgical complications such as bleeding, thromboembolism function, and increased risk of infection.

Still another solution for maintaining the existing natural heart as the pumping device involves enveloping a substantial portion of the natural heart, such as the entire left and right ventricles, with a pumping device for rhythmic compression. That is, the exterior wall surfaces of the heart are contacted and the heart walls are compressed to change the volume of the heart and thereby pump blood out of the chambers. Although somewhat effective as a short term treatment, the existing pumping devices have not been suitable for long term use.

Typically, with such compression devices, heart walls are concentrically compressed. A vacuum pressure is then needed to overcome cardiac tissue/wall stiffness, so that the compressed heart chambers can return to their original volume and refill with blood. This "active filling" of the chambers with blood limits the ability of the pumping device to respond to the need for adjustments in the blood volume pumped through the natural heart, and can adversely affect the circulation of blood to the coronary arteries. Furthermore, natural heart valves, between the chambers of the heart and leaching into and out of the heart, are quite sensitive to wall distortion and annular distortion. The compressive movement patterns that reduce a chamber's volume and distort the heart walls may not necessarily facilitate valve closure (which can lead to valve leakage).

Therefore, mechanical pumping of the heart, such as through mechanical compression or distortion of the ventricles, must address these issues and concerns in order to establish the efficacy of long term mechanical or mechanically-assisted pumping. Specifically, the ventricles must rapidly and passively refill at low physiologic pressures, and the valve functions must be physiologically adequate. The myocardial blood flow of the heart also must not be impaired by the mechanical device. Still further, the left and right ventricle pressure independence must be maintained within the heart.

The present invention addresses the issues of heart wall stiffness and the need for active refilling by assisting in the bending (i.e., indenting, flattening, twisting, etc.) of the heart walls, rather than concentrically compressing the heart walls. Because of the mechanics of deformation in hearts having proportions typical in heart failure (specifically, wall thickness/chamber radius ratios), the deformation from bending and the subsequent refilling of the heart requires significantly less energy than would the re-stretching of a wall that has been shortened to change the chamber volume a similar amount. The present invention facilitates such desirable heart wall bending and specifically protects the heart wall during such bending.

Another major obstacle with long term use of such pumping devices is the deleterious effect of forceful contact of different parts of the living internal heart surface (endocardium), one against another, due to lack of precise control of wall actuation. In certain cases, this coaptation of endocardium tissue is probably necessary for a device that encompasses both ventricles to produce independent output pressures from the left and right ventricles. However, it can compromise the integrity of the living endothelium.

Mechanical ventricular wall actuation has shown promise, despite the issues noted above. As such, devices have been invented for mechanically assisting the pumping function of the heart, and specifically for externally actuating a heart wall, such as a ventricular wall, to assist in such pumping functions.

Specifically, U.S. Pat. No. 5,957,977, which is incorporated herein by reference in its entirety, discloses an actuation device for the natural heart utilizing internal and external support structures. That patent provides an internal and external framework mounted internally and externally with respect to the natural heart, and an actuator or activator mounted to the framework for providing cyclical forces to deform one or more walls of the heart, such as the left ventricular wall. The invention of U.S. patent application Ser. No. 09/850,554, which is also incorporated herein by reference in its entirety, further adds to the art of U.S. Pat. No. 5,957,977 and specifically sets forth various embodiments of activators or actuator devices which are suitable for deforming the heart walls and supplementing and/or providing the pumping function for the natural heart.

When heart wall actuation systems like those noted above are utilized, the heart wall is actuated by being indented and/or deformed proximate a chamber of the heart to change the volume of the chamber. When actuated or indented in such a way, a heart wall, or at least portions of the wall may have a tendency to take on shapes which are not desirable from a physical standpoint. More specifically, the heart walls may have a tendency to become overly distended, or take on sharp curvatures, in certain areas based upon the indentation of those walls in other areas. Such unnatural shaping of the heart tissue may be damaging to the tissue. Therefore, when utilizing a heart wall actuation system, one issue to be addressed is the shape of the walls when the system is actuated, and the variance of that shape from the natural shape that the heart would assume when pumping normally.

It is therefore an objective of the present invention to assist in the operation of heart wall actuation systems with the natural heart.

It is a further objective to reduce and prevent unnatural distortion of the heart and its components during activation with a heart wall actuation system.

It is still another objective of the present invention to provide long term actuation and assistance for the heart by reducing unnatural stress on the heart during such actuation.

These objectives and other objectives and advantages of the present invention will be set forth and will become more apparent in the description of the invention below.

SUMMARY OF THE INVENTION

The present invention addresses the above objectives and other objectives by providing an actuation system for assisting the operation of the natural heart which utilizes a shape-limiting element configured for being positioned proximate a heart wall to control the shape of the heart when it is actuated. The shape-limiting element is operable for bending or flexing to a predetermined curvature or multiple curvatures when the heart wall is acted upon and maintaining those predetermined curvatures to control the shape of the actuated heart and limit any undesirable tensile or compressive strain induced upon the heart tissue. In one embodiment, the shape-limiting element is utilized within an actuation system comprising a framework for interfacing with the natural heart, which includes an element configured for being anchored to tissue of the heart. An actuator element is adapted for being coupled to the framework and is configured for extending proximate a portion of a heart wall and acting on the heart wall to effect a change in the shape of the heart. The shape-limiting element may be coupled to the actuator element such that the forces on the heart wall are also forces which vary the shape of the shape-limiting element.

In one embodiment of the invention, the shape-limiting element comprises a plurality of discrete links which are positioned to form an elongated band. The links are hingedly coupled together and hinge with respect to each other so the band may flex or bend and change its shape. At least two of the adjacent links are shaped to interfere with each other when the links are hinged in a direction for a predetermined distance, to thereby limit further hinging and to maintain a predetermined curvature of the band. In a more specific embodiment, the adjacent links include projections which extend outwardly from a longitudinal axis of the band. The projections are configured for interfering with each other upon flexing or bending of the band, and the resultant hinging of the links in order to prevent flexing of the band past a certain limit. The projections might be configured to further provide one predetermined curvature when the band is flexed in one direction, and to provide another predetermined curvature when the band is flexed in the other direction.

In accordance with another embodiment of the present invention, the shape-limiting element is in the form of a flexible belt having projections thereon which interfere with each other and limit the flexing of the belt to a predetermined curvature.

In another embodiment of the invention, one or more tethers are utilized to span between links of a hinging band, or along the flexible belt. The tethers, which are fixed to the band or belt at certain positions, have limited extensibility to thereby limit the hinging or flexing of the element to a predetermined amount or distance to thereby maintain a predetermined curvature of the band when the heart is actuated.

In another embodiment of the invention, a band of discrete hinging links utilizes a rigid stop element which spans between the links to engage the links and limit their hinging to a predetermined amount or distance. Individual links will hinge or pivot until they encounter the rigid stop element which generally prevents further hinging. The rigid stop elements might be individual elements which are coupled between the links on one or both surfaces of the band. Alternatively, stop elements on both sides of the band may be coupled together to form a unitary structure which may be hingedly coupled with the discreet links of the band.

In an alternative embodiment of the invention, a tubular stop element, generally coaxial with the longitudinal axis of the band, may surround portions of at least two links. The stop elements form upper and lower stop portions which are figured to engage the links and limit their hinging to thereby maintain a predetermined curvature of the band, once the band is bent or flexed a certain amount or distance.

In another embodiment of the invention, a helical spring is utilized in combination with shape-limiting or curvature limiting structures to limit the shape of the helical spring and the overall shape of the heart. In one example, a sheath over the helical spring provides such shape limiting of the helical spring. In another example, discrete links, interlaced between the coils of the helical spring provide the shape limiting.

Further details of the invention are set forth below in the Detailed Description of the Invention.

BRIEF DESCRIPTION OF THE DRAWINGS

The accompanying drawings, which are incorporated in and constitute a part of this specification, illustrate embodiments of the invention and, together with a general description of the invention given below, serve to explain the principles of the invention.

DETAILED DESCRIPTION OF THE EMBODIMENTS

The present invention may best be described in the context of the natural human heart, and accordingly, the heart structure is discussed briefly below. Furthermore, the system of one embodiment, is utilized with an actuator which is coupled to a framework which cooperates with the human heart. One suitable actuator and framework for practicing the invention is disclosed in greater detail in U.S. Pat. No. 5,957,977, which is incorporated herein by reference in its entirety. Another actuation system suitable for use with the present invention is set forth in U.S. patent application Ser. No. 09/850,554, which is incorporated herein by reference in its entirety. A brief overview of the heart and a suitable heart wall actuation system for practicing the invention is set forth below. However, the present invention and its benefits are not limited to the disclosed actuation system or framework. Other actuation systems and/or frameworks will also be suitable for practicing the invention.

Figure 1:
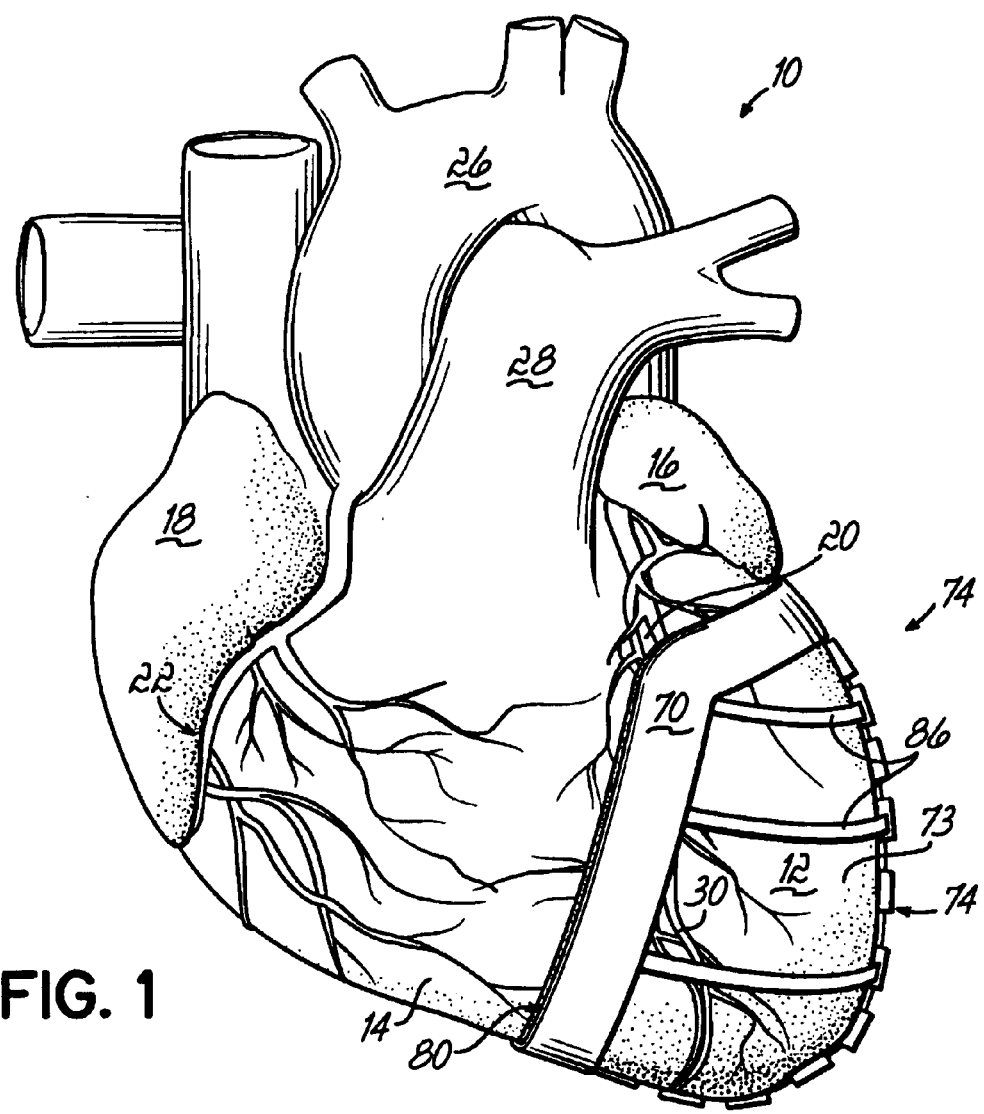
FIG. 1 is a perspective view of a human heart utilizing one embodiment of the invention.

Referring now to FIG. 1, a natural human heart 10 is shown in perspective with a portion of a framework for an actuation system. The heart 10 has a lower portion comprising two chambers, namely a left ventricle 12 and a right ventricle 14, which function primarily to supply the main pumping forces that propel blood through the circulatory system, including the pulmonary system (lungs) and the rest of the body, respectively. Heart 10 also includes an upper portion having two chambers, a left atrium 16 and a right atrium 18, which primarily serve as entryways to the ventricles 12 or 14, and also assist in moving blood into the ventricles 12 or 14. The interventricular wall or septum of cardiac tissue separating the left and right ventricles 12 and 14, is defined externally by an interventricular groove 20 on the exterior wall of the natural heart 10. The atrioventricular wall of cardiac tissue separating the lower ventricular region from the upper atrial region is defined by atrioventricular groove 22 on the exterior wall of the natural heart 10. The configuration and function of the heart is known to those skilled in this art.

Generally, the ventricles are in fluid communication with their respective atria through an atrioventricular valve in the interior volume defined by heart 10. More specifically, the left ventricle 12 is in fluid communication with the left atrium 16 through the mitral valve, while the right ventricle 14 is in fluid communication with the right atrium 18 through the tricuspid valve. Generally, the ventricles are in fluid communication with the circulatory system (i.e., the pulmonary and peripheral circulatory system) through semi-lunar valves. More specifically, the left ventricle 12 is in fluid communication with the aorta 26 of the peripheral circulatory system, through the aortic valve, while the right ventricle 14 is in fluid communication with the pulmonary artery 28 of the pulmonary, circulatory system through the pulmonic or pulmonary valve.

The heart basically acts like a pump. The left and right ventricles are separate, but share a common wall, or septum. The left ventricle has thicker walls and pumps blood into the systemic circulation of the body. The pumping action of the left ventricle is more forceful than that of the right ventricle, and the associated pressure achieved within the left ventricle is also greater than in the right ventricle. The right ventricle pumps blood into the pulmonary circulation, including the lungs. During operation, the left ventricle fills with blood in the portion of the cardiac cycle referred to as diastole. The left ventricle then ejects any blood in the part of the cardiac cycle referred to as systole. The volume of the left ventricle is largest during diastole, and smallest during systole. The heart chambers, particularly the ventricles, change in volume during pumping.

By way of a non-limiting example, the present invention is discussed in terms of embodiments that are used to primarily assist in the actuation and operation solely of the left ventricular portion of the heart 10. However, it is noted that the present invention can also be used to assist in the actuation and operation of other portions of the natural heart 10, such as individual atria, the right ventricular portion of the heart 10, or simultaneously both atria or both ventricles.

In accordance with illustrating an example of use of the invention with the left ventricular portion of the heart, one possible framework and actuator system are discussed which are positioned on the exterior surface or epicardium of the left ventricle. The invention may also be used with other chambers of the heart.

Figure 2A:
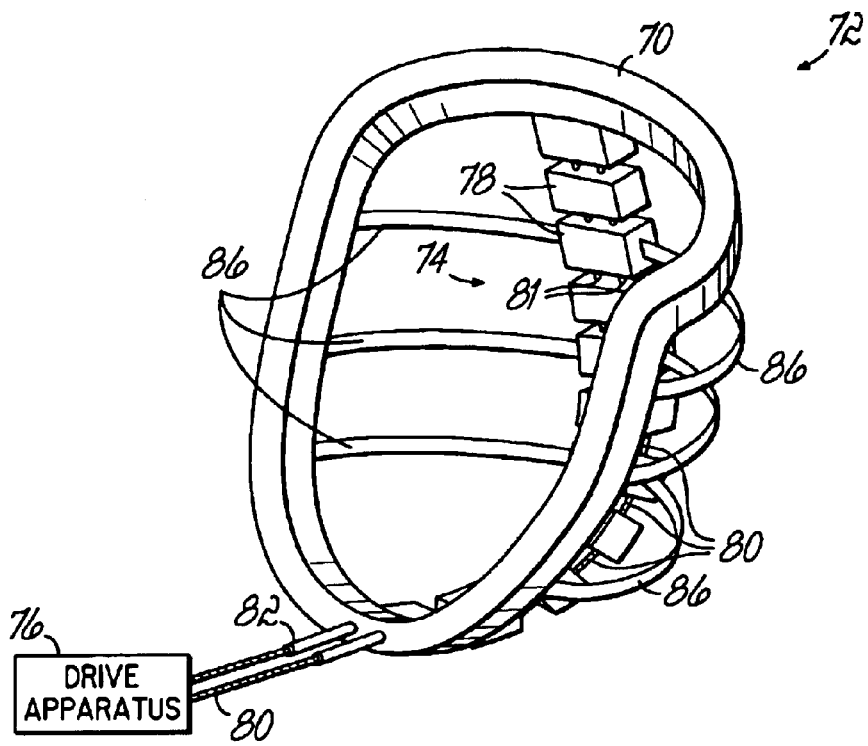
FIGS. 2A and 2B are perspective views illustrating an actuation system incorporating the invention in a relaxed state, and in an actuated state, respectively.
Figure 2B:
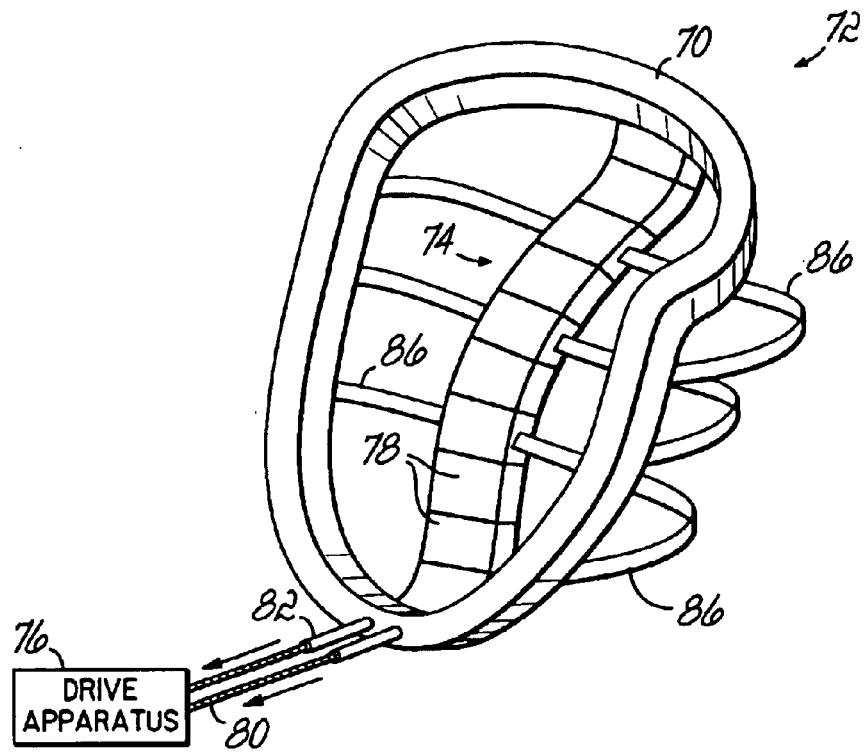

Part of the framework for an actuation system is illustrated in FIGS. 1, 2A, and 2B by reference numeral 70, which refers to an external component or yoke of the framework. The framework also includes one or more internal framework elements (not shown) including an internal stent to which the external yoke or external framework element 70 is fixed by transmural cords which extend through walls of the heart. The internal stent is sized and configured for placement within the interior volume of the natural heart 10, generally alongside the right side of the interventricular septum. The stent also includes at least two separate ring structures for positioning proximate the valve annuli of the left side of the heart. Further details of one suitable framework are set forth in U.S. Pat. No. 5,957,977.

As noted above, the framework includes external yoke 70, for placement around a portion of the exterior surface or epicardium of a natural heart 10. The generally stirrup-shaped yoke 70 in the illustrated embodiment restricts free motion of the natural heart 10 so that the natural heart 10 can be actuated and assisted. Yoke 70 also acts as an anchor or base for an appropriate actuator system for use with the invention. In one embodiment, the yoke 70 is between about 1 and 2 cm wide and includes a semi-rigid collar portion, preferably made of either a solid polymer of appropriate mechanical behavior, such as polypropylene or polyacetal, or a composite of metal (stainless steel or pure titanium) band or coil spring elements, polymer fabric and fiber (e.g. polyester knit) and soft elastomer, for providing rigidity to the yoke 70. Additionally, the yoke 70 may include a gel-filled cushion portion 80 that is positioned immediately adjacent the exterior surface (epicardium) of the natural heart 10 for providing equalized pressure over the irregularities in the epicardial surface of the heart 10, and any of the coronary arteries 30 within a region under the yoke 70. Preferably, the yoke 70 is sized and configured for placement adjacent at least a portion of the atrioventricular groove 22, and simultaneously adjacent at least a portion of the anterior and posterior portions of the interventricular groove 20, and most preferably, adjacent at least a substantial portion of the anterior and posterior portion of the interventricular groove 20, as shown in FIG. 1.

General alignment of the yoke 70 with interior framework elements is maintained by at least one transmural cord (not shown), and preferably, a plurality of cords that penetrate the walls of the natural heart 10 and connect to the internal stent and one or more of the internal rings, as discussed in U.S. Pat. No. 5,957,977.

FIGS. 2A and 2B illustrate one embodiment of the present invention which includes elements of the framework described above, and specifically includes the external framework element or yoke 70, anchored to tissue of the heart. The actuation system 72 includes an actuator element which is configured to engage or extend proximate to or along a heart wall exterior surface, or epicardial surface 73 of the heart 10 (See FIG. 1). The actuation system 72 has a relaxed state as illustrated in FIG. 2A, wherein the actuator element, such as an actuator band 74 will generally follow the distended curvature of a heart wall portion of the relaxed or diastolic heart. The actuation system also has an actuated state, as illustrated in FIG. 2B, wherein the band 74 engages and acts on the outer surface of the heart wall and effects a shape and volume change of a portion of the heart, such as the left ventricle by indenting or deforming the heart wall. The shape of the actuated band 74 will determine the type of shape of the heart indentation and the resultant forces on the heart. In the embodiment of the invention illustrated in FIGS. 2A and 2B, the actuation system thereby comprises an actuator band 74 which is selectively movable between the relaxed state (FIG. 2A) and actuated state (FIG. 2B). The actuator band 74 is operable, when in the actuated state, to assume a predetermined shape and/or curvature, and thereby indent a portion of the heart wall to effect a change in the shape of the heart and thereby effect a reduction in the volume of the heart chamber. A drive apparatus 76 is coupled to the actuator band and is operable for selectively moving the actuator band between the relaxed and actuated states to achieve the desired assistance of the natural heart.

Referring to FIG. 2A, the actuation system utilizes an actuator band 74 comprising a plurality of juxtaposed blocks 78 which may be drawn together by drawing cords 80, which pass through apertures 81 in the blocks, and through associated sheaths 82, to make the band 74 form a predetermined shape and thereby act on the heart surface 73 to effect a change in the shape of the heart.

In accordance with one aspect of the present invention, the shape of the heart is controlled by shape-limiting elements 86 which are also configured for being positioned proximate a heart wall. The shape-limiting elements will generally be positioned proximate the actuator element. In the embodiment illustrated in FIGS. 2A and 2B, the shape-limiting elements 86 cooperate with the actuator element or band 74 and are actually coupled thereto. The shape-limiting elements are operable for bending or flexing to assume a predetermined curvature or shape when the heart wall is acted upon by band 74. The shape-limiting elements 86 maintain the predetermined curvature or shape and control the shape of the heart so that the heart is not overly distended, and so that the heart will not take on shapes or curves which are detrimental to the heart wall and the tissue forming the heart wall.

In one embodiment of the invention, the shape-limiting elements are configured as elongated bands which extend along a wall of the heart. The bands are flexible and may be bent or flexed when a force is applied thereto, such as by an actuator element 74. However, the bands are constructed to only bend or flex a certain amount or a certain distance, and then to resist any further bending or flexing. That is, various portions of the flexible band will take on or assume predetermined curvatures when bent or flexed. Once the predetermined curvature is attained, the curvature-limiting band will resist any further bending or flexing in that particular direction. In accordance with one aspect of the present invention, different portions or sections of the band may have different predetermined curvatures or shapes when bent. That is one portion might bend past the curvature amount of another portion of the band. Furthermore, the band might flex in one direction a greater amount than it flexes in another direction, so that, depending upon the direction of flex, the band will take one shape, or have one predetermined curvature which is different than the shape or predetermined curvature achieved when the band is flexed in the other direction.

As noted above, the shape-limiting elements, as illustrated herein, are not specifically confined to use with a "string-of-blocks" actuator element 74, which is shown by way of example. As illustrated in FIGS. 2A and 2B, the shape-limiting elements 86 are coupled to the actuator element 74 for moving with the actuator element and being bent or flexed by the forces of the actuator element. Alternatively, they might be mounted and positioned proximate the heart independently of the actuator element.

Figure 3:
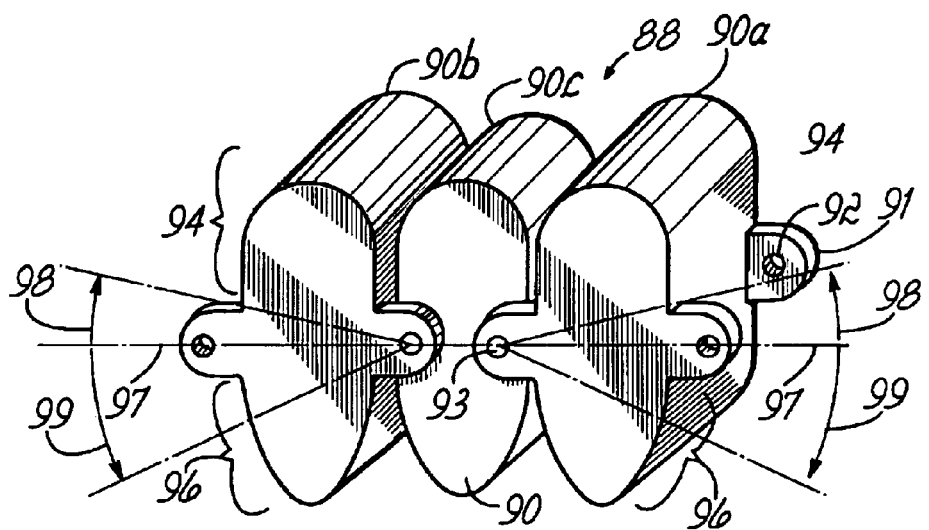
FIG. 3 is a sectional view of one embodiment of a shape-limiting element in accordance with the principles of the present invention.

FIG. 3 illustrates one embodiment of a shape-limiting element in accordance with the principles of the present invention. FIG. 3 shows a perspective view of a small section of an elongated band 88 which comprises a plurality of distinct links which are positioned, generally end-to-end or side-by-side to form an elongated band. The links are hingedly coupled together to hinge with respect to each other for varying the shape of the band. For example, the links 90a, 90b, in FIG. 3 have tabs 91 with apertures 92 formed therethrough for receiving hinge pins 93 such that the links are hingedly coupled together to hinge with respect to each other for varying the shape of the band. The links include projections or projection sections 94, 96 which extend outwardly from a longitudinal axis of the band indicated by reference numeral 97. When the adjacent links, such as links 90a and 90c are hinged a certain distance in a direction, such as the direction indicated by reference arrows 98, the links interfere with each other to limit further hinging and to maintain a predetermined shape and/or curvature of the band. That is, when the links are hinged in the direction 98, the projections 94 will touch each other and prevent further hinging, to limit the curvature of the bands. In that way, the actuated or flexed band will maintain a predetermined curvature, and when positioned along the side of the heart, the band 88 will control the shape of the heart when the heart wall is actuated by the actuator mechanism.

As illustrated in FIG. 3, the links 90a, 90b, and 90c have projections 94, 96 which extend on both sides of a longitudinal axis 97. Therefore, when the adjacent links 90a, 90c are hinged in an opposite direction as indicated by reference numeral 99, projections 96 will interfere with each other. When the adjacent links are hinged a predetermined amount or distance, further hinging is thereby limited to maintain a predetermined curvature in the band in that direction as well. Therefore, the adjacent links are shaped to interfere with each other when hinged in both the first direction and also in an opposite direction. Alternatively, the links might be configured only to significantly interfere with each other when the band is flexed in one direction. As will be appreciated, each of the adjacent links will generally interfere with the other adjacent links to limit hinging past a certain point and thereby maintain the predetermined curvature of the band. That is, band 88 will flex and bend for predetermined distances in certain sections of the band to form a shape and to maintain predetermined curvatures. The band will then no longer significantly flex or bend past a predetermined curvature, and the predetermined curvature of the band will be maintained to maintain a desired shape of the heart.

In accordance with another aspect of the present invention, the adjacent links may be further configured to maintain one predetermined curvature when hinged in one direction, and to maintain a different predetermined curvature when hinged in an opposite direction. Referring again to FIG. 3, the projections 96 illustrated for the links are thinner than the projections 94. In that way, the hinged links, specifically projections 96, will have to hinge a greater amount in one direction before they interfere with each other, than will the projections 94 (which are generally illustrated as being wider than the protrusions 96) when the band is hinged in an opposite direction. As such, different predetermined curvatures are allowed, depending upon which direction the actuator band is flexed or bent.

Figure 11:
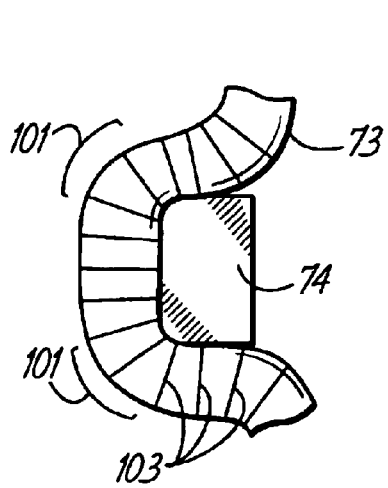
FIG. 11 is a sectional, cross-sectional view of a heart wall actuated by an actuation system without utilizing the shape-limiting invention.
Figure 12:
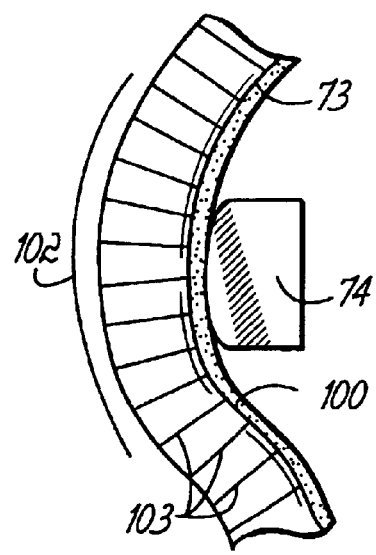
FIG. 12 is a sectional, cross-sectional view of a heart wall utilizing the present invention.

Turning now to FIGS. 11 and 12, a schematic view is shown of heart wall surface 73 being actuated by an actuator element 74 with and without the shape-limiting of the present invention. Specifically, FIG. 11 shows significant curves in the heart wall surface 73 made by the actuator element 74 when the shape of the heart is not controlled. FIG. 12, on the other hand, shows a system utilizing a shape-limiting element 100 which maintains a predetermined curvature and controls the shape of the actuated heart. To that end, the curvature (mathematically defined as the inverse of the radius of curvature) associated with the curves 101, as illustrated in FIG. 11, is significantly lessened for the curve 102, as illustrated in FIG. 12. In that way, significantly unnatural shaping of the heart is prevented, and damage to heart tissue is also prevented.

Figure 5:
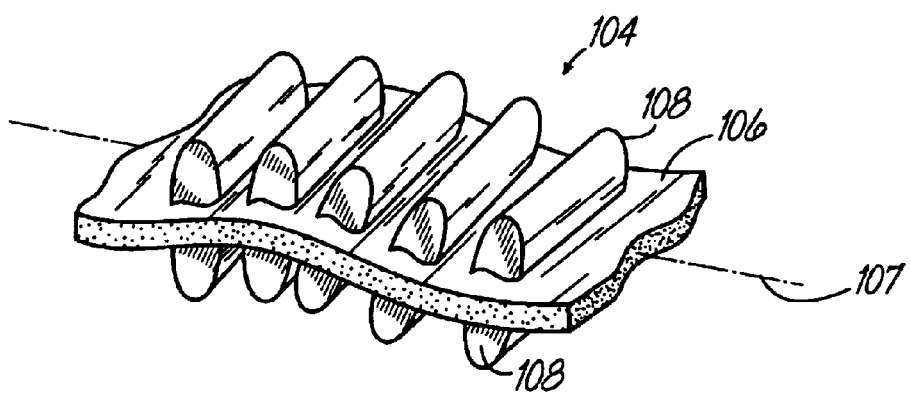
FIG. 5 is a sectional view of another embodiment of a shape-limiting element in accordance with the principles of the present invention.

FIG. 5 illustrates an alternative embodiment of the shape-limiting element of the invention. The element is in the form of a band 104, including a flexible belt 106, with a plurality of protections, or projection portions 108, which extend outwardly from a longitudinal axis 107 of the band. As discussed above with respect to FIG. 3, the band 106 is flexible, and can flex or bend in opposite directions for a predetermined amount to form a predetermined shape and curvature, such as when the heart wall is acted upon by an actuator element. The projections 108, which are shown on both sides of the belt 106, in the embodiment of FIG. 5, interfere with each other when the belt is flexed a predetermined amount to limit further flexing and to maintain a predetermined curvature of the band. In that way, the shape of the heart may be controlled when a wall of the heart is being actuated by an actuation system. The belt 106 may be formed of a suitable flexible material, such as a strip of soft, solid polymer, leather, fabric, and so forth. The projections 108 may be formed of a suitable sufficiently hard material, such as stainless steel 316, or CP titanium, so that the projections properly interfere with each other to prevent further flexing or hinging of the band as discussed above with band 88. Similarly, the links 90 of band 88 may be formed of such materials.

Figure 4:
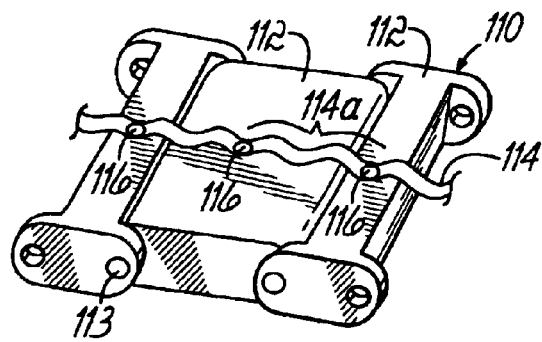
FIG. 4 is a sectional view of another embodiment of a shape-limiting element in accordance with the principles of the present invention.

In accordance with another aspect of the present invention, the predetermined curvature of the shape-limiting element may be maintained by tether structures spanning between at least two adjacent links, rather than mechanical interference between the links. Turning to FIG. 4, a band 110 is illustrated, having multiple discreet links 112 which may hinge with respect to each other on pins 113. A tether 114 spans between at least two adjacent links. The tether 114 has limited extensibility to limit hinging when the adjacent links 112 are hinged in a direction a predetermined amount or distance. To that end, the tether 114 may be fixed at points 116 to a side of the band 110. Alternatively, another, similar tether might be positioned on the other side of the band 110. As is readily understood, when the links 112 are hinged in one direction to extend a portion of the tether 114, such as tether portion 114a, that portion will reach its maximum extended length and then limit further hinging of the links in a particular direction. It is the tether on the outside radius of the curved band which limits further action, rather than the tether on the inside radius. By tethering various of the links of the band 110 together, the predetermined curvature of the band may be maintained. FIG. 4 illustrates a single tether 114 extending along the length and coupled at multiple points 116. Alternatively, individual small tether portions 114a might be individually attached between the links 112, rather than a single long tether. With tethering on both sides, the predetermined curvature of the band may be controlled when the band is bent or flexed in both directions.

Figure 6:
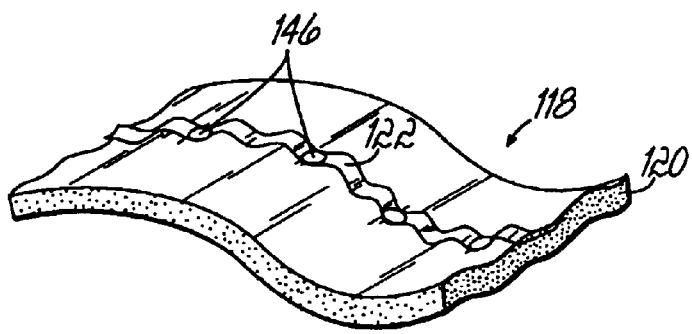
FIG. 6 is a sectional view of another embodiment of a shape-limiting element in accordance with the principles of the present invention.

FIG. 6 illustrates another alternative embodiment of a shape-limiting element, wherein a band 118 includes a belt 120 and a tether 122 which is coupled at various points 123 along the length of the belt. When the belt is flexed or bent in a direction, tether 122 has limited extensibility and will only allow the belt 120 to bend to a predetermined curvature, and will then maintain that predetermined curvature and generally prevent further bending in order to control the shape of the heart that is being actuated.

The tethers 114, 122, as illustrated in the drawings, are in the form of thin bands. However, the tethers might include alternative structures, such as cord, cables and chains. Multiple tethers or a single tether are fixed to the surfaces of a band or belt, and fixed in intervals 146 to such surfaces. At the extent of flexion of the band or belt between tether fixation points. The corresponding segment of tether becomes taut and the bert or band flexion is limited to maintain a predetermined curvature.

Figure 7:
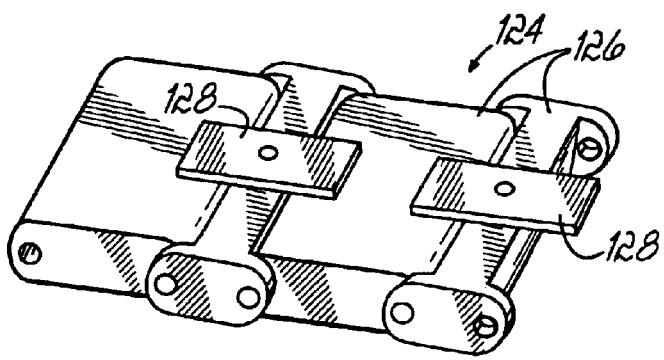
FIG. 7 is a sectional view of another embodiment of a shape-limiting element in accordance with the principles of the present invention.

Turning now to FIG. 7, a band 124, having multiple links 126 is shown similar to the band of FIG. 4. The multiple links or other discrete elements are positioned to form an elongated band, and the links hinge with respect to each other for varying the shape of the elongated band. For maintaining a predetermined curvature, band 124 utilizes a plurality of rigid stop elements 128 which are fixed to the band to span between at least two adjacent links. The stop elements 128 are configured to engage the links and limit their hinging when the adjacent links are hinged in one direction a predetermined amount. This thereby maintains a predetermined curvature of the band. In the embodiment illustrated in FIG. 7, a single stop element 128 fixed to one link 126 also spans across and engages adjacent links on either side of the link to which the stop element is fixed. The stop element may be shaped and configured to provide a desired amount of flexing or bending of the band, to prevent any further flexing or bending past the predetermined curvature, as discussed above. The stop elements 128 might be positioned on one or both surfaces of the band 124.

Figure 8:
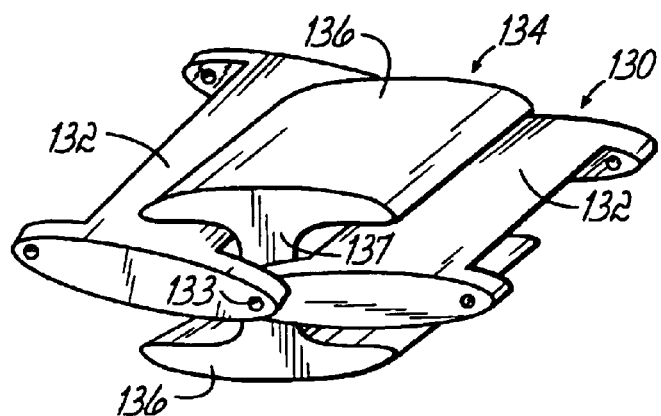
FIG. 8 is a sectional view of another embodiment of a shape-limiting element in accordance with the principles of the present invention.

FIG. 8 illustrates another alternative embodiment of a shape-limiting element wherein band 130 includes discrete links 132 which hinge with respect to one another, such as at a hinge point 133. Band 130 between the links 132 incorporates a structure 134 which incorporates stop elements 136 on both sides of the band, and which couples the stop elements 136 together. The structure 134 has an I-beam shape in cross-section. The center portion 137 between the stop elements 136 may be coupled to the links 132, such as by being hingedly coupled with the links, or may float freely between the links. In any case, when the links are hinged together and the band is bent or flexed, the links 132 will engage the stop structures 136 and be prevented from further hinging past a predetermined curvature for the band, in accordance with one aspect of the present invention.

Figure 9:
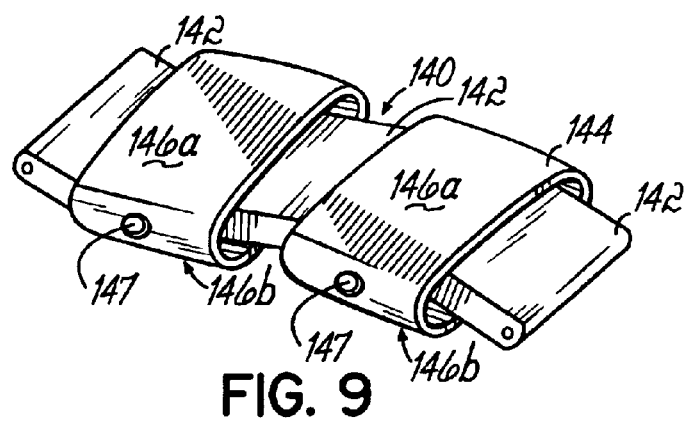
FIG. 9 is a sectional view of another embodiment of a shape-limiting element in accordance with the principles of the present invention.
Figure 10:
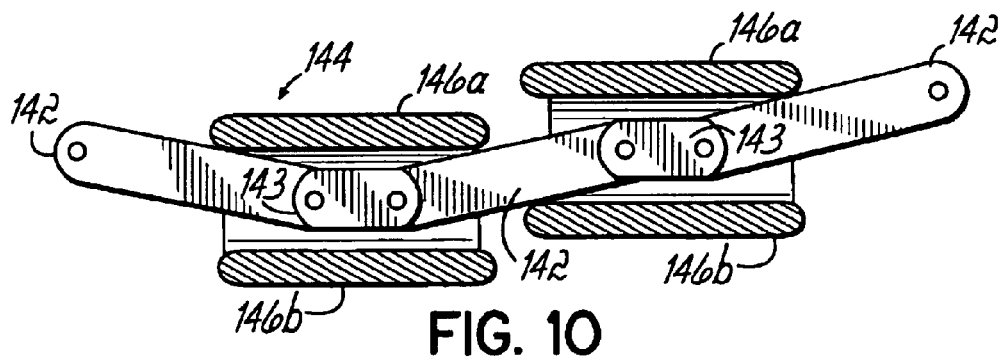
FIG. 10 is a sectional cross-sectional view of the shape-limiting element of FIG. 9.

FIGS. 9 and 10 illustrate another embodiment of a stop structure which might be utilized with a shape-limiting element, for achieving the desired predetermined curvature and flexion limitation for the shape-limiting element.

FIGS. 9 and 10 illustrate a perspective and cross-sectional view, respectively, of a band 140 comprising a plurality of links 142, such as the link structures as illustrated in FIGS. 4 and 7. Rather than having stop structures individually positioned proximate sides of the band, a tubular-shaped stop element 144 is utilized, which forms an opposing top stop portion 146a and a bottom stop portion 146b. The tubular-shaped element 144 cooperates to prevent hinging of the links 142 beyond a predetermined amount to thereby set and maintain a predetermined curvature for the band when it is flexed or bent in one or more directions. The tubular stop element 144 might be fixed in place, such as by being hinged with the center linkage element 143 at a hinge point 147, as illustrated in FIGS. 9 and 10. Alternatively, rather than having a specific linkage element, the links 142 may be directly hinged to each other on a hinge pin that is mounted to the tubular stop element 144 at hinge point 147. Referring to FIG. 10, when the links 142 hinge past a certain point, various of the links will engage the tubular stop element 144 and generally be prevented from hinging further in a particular direction.

In accordance with one advantage of the present invention, the imposed curvature of a heart wall, which is deformed by a heart wall actuation system and an actuator element, cannot exceed a given limit. The curvature "k" is defined as the inverse of the radius of curvature with units of length$^{-1}$. By preventing the curvature (k) from exceeding a given limit, the radius of curvature is prevented from being reduced below a given limit, so that sharp curvature points of the deformed or actuated heart wall are avoided.

This is a particular advantage, because the maximum tensile or compressive strain induced in the heart wall tissue is a direct consequence of the thickness of the heart wall and the induced curvature. Any excessive tensile or compressive strain on the heart wall may cause tissue disruption or other associated damage.

Referring to FIGS. 11 and 12, various crossing lines 103 are illustrated through the heart wall 73. The change and separation between the various crossing lines 103, at varying positions along the heart wall, indicate the imposed tensile and/or compressive strain at those points. As may be seen between FIGS. 11 and 12, the maximum tensile strain in the inner layers of portions of the heart wall 73 adjacent the corners of the actuator element 74, are much greater without a shape-limiting element 100 (FIG. 11), than with a shape-limiting element (FIG. 12).

Figure 13A:
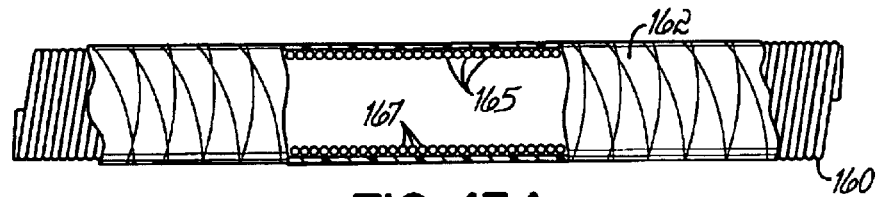
FIGS. 13A, 13B are front views of an alternative embodiment of the invention shown at rest and bent, respectively.
Figure 13B:
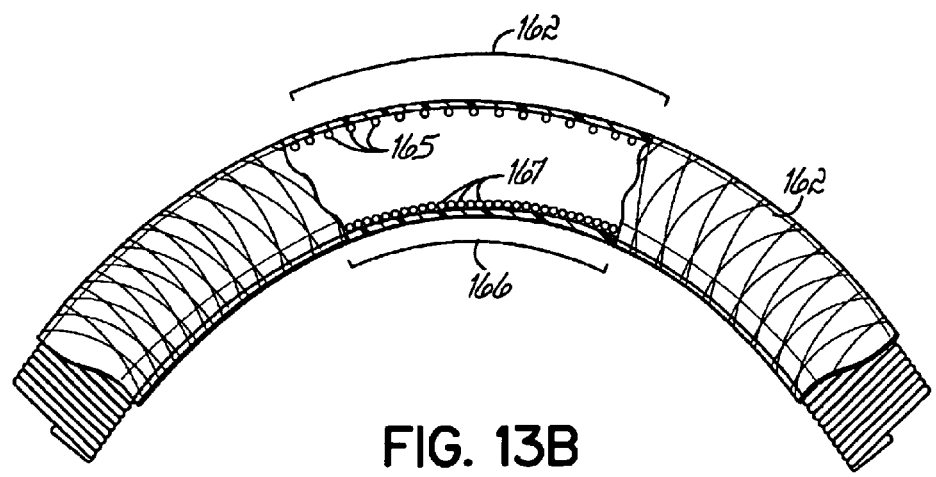

In accordance with another aspect of the present invention, flexible spring structures, combined with additional structures to limit their flexing or bending, may be utilized. Such structures may be used as shape-limiting elements as discussed above. Referring to FIGS. 13A and 13B, a flexible spring 160 is shown and includes closely wound or tightly wound coils or coil turns. Spring 160 may be made of high fatigue metal, such as titanium, or other suitable compositions. Also, the spring might be constructed with standard circular turns or coils as illustrated in FIGS. 13A and 13B. Alternatively, as illustrated in FIGS. 16A–E and as illustrated and further discussed here and below, other coil shapes might be used.

In combination with spring structure 160 is an outer sheath 162, which is woven or otherwise formed around the spring structure 160. The sheath 162 operates to restrict the bending or flexibility of the inner core spring structure 160.

The spring structure 160 may be bent until the sheath 162 reaches its maximum elongation. The sheath is specifically woven or formed to allow bending of the spring structures 160 within a range designated by the curvature desired. Therefore, curvature of the spring structure is limited.

More specifically, referring to FIG. 13B, when the spring structure is bent, a portion 164 thereof becomes more convex (or less concave) and the distance between the individual coil sections 165 increases. The distance between the coil sections 165, and therefore the shape of the spring structure 160 at area 164, is limited by the restriction provided by sheath 162. Similarly, a portion or area 166 of the spring structure 160, indicated by coil sections 167, becomes generally more concave (or less convex) wherein the spring structure in that area remains generally the same length as it was prior to being bent as illustrated in FIG. 13A. The outer sheath 162 provides generally a tethering action and when any part of the sheath reaches its maximum length (e.g., all component fibers within a woven sheet are straightened to their maximum length), further bending or flexing is generally prevented. Generally, the sheath is constructed so that substantial deformation or breaking of its fibers or other components will not occur with the forces that are expected in its use. Referring to FIG. 1, the structure such as illustrated in FIGS. 13A and 13B might be utilized as a shape-limiting element 86 as shown in FIG. 1.

Figure 14A:
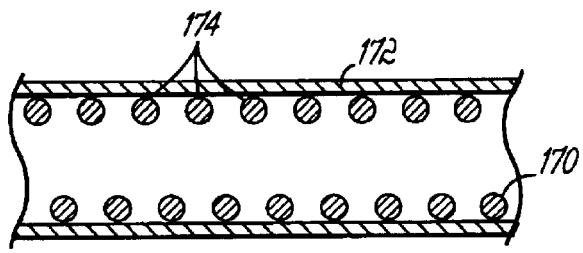
FIGS. 14A and 14B are front views of another alternative embodiment of the invention shown at rest and bent, respectively.
Figure 14B:
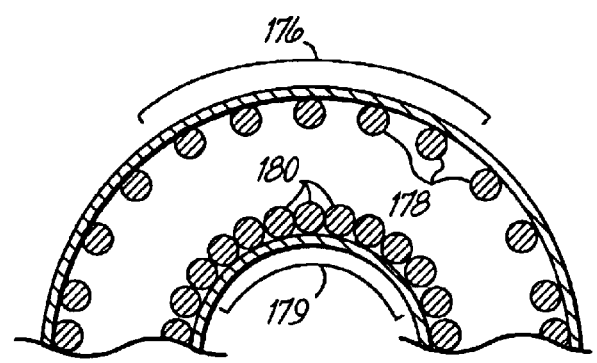

FIGS. 14A and 14B illustrate another alternative embodiment of a spring structure 170, in combination with a sheath 172. The spring structure 170 has loosely wound coils 174. It is also formed of a suitable material, such as CP titanium or stainless steel or a shape memory composition. The spring structure 170 is encased, at least partially, in a sheath 172 which may be similarly formed as the sheath 162 discussed above. When a bending moment is imposed on the spring structure 170, a convex surface 176 of the sheath 172 is already tightened and will not permit the convex coil sections 178 to generally separate any further. This generally prevents significant elongation of the convex portion of the spring. However, in a concave portion 179 of the spring structure illustrated by coil sections 180, the coil sections 180 may be drawn closer together, thereby effectively shortening the coiled concave portion 179. Generally when the coiled sections 180 are in contact with each other, no further significant shortening of the concave portion 179 will occur without either compressive deformation of the coil sections 180 or tensile deformation or breaking of the sheath 176. The structure may be designed and build for specific minimum radius (or, equivalently, maximum curvature) limits by selection of wire gauge, inter-coil coil gaps after sheath placement, and elastic characteristics of the sheath, and initial sheath tension imposed by the compressed spring structure.

Figure 15:
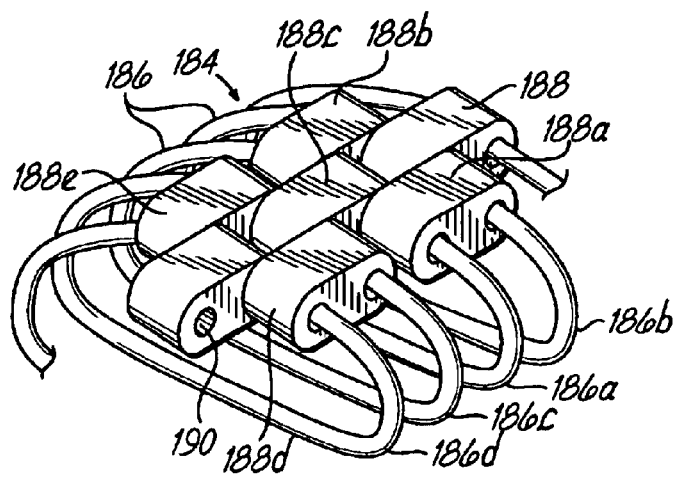
FIG. 15 is a partial perspective view of another embodiment of the invention.

In an alternative embodiment of the invention as illustrated in FIG. 15, a somewhat loosely wound helical spring structure 184 might be constrained along a side or portion thereof to maintain a specific length or curvature. Referring to FIG. 15, the coil structure 184 having various coil turns 186 is utilized in combination with rigid links 188 which connect adjacent coils along one side, or section, or aspect of the coil structure 184. The links are formed of a suitable rigid material, such as a high-strength polymer (e.g., polyacetal or ultrahigh molecular weight polyethylene (UHMWPH)), or of a highly rigid material such as a metal (e.g., stainless steel or CP titanium or other biocompatible alloy). The links 188 are formed so that they have appropriate apertures 190 through which the coil turns 186 may pass. The apertures 190 may be angled to address the appropriately angled pitch of the coil turns. As illustrated in FIG. 15, adjacent coils, such as coils 186a and 186b are kept at a fixed distance apart, along one aspect of the spring structure, by one or more of the links 188. In one embodiment, the links will be staggered.

For example, links 188a and 188b might couple together turns 186a and 186b. Similarly, link 188c might couple together turns 186a and 186c. Further, links 188d and 188e might couple together coil turns 186c and 186d. Similarly, the pattern might be repeated along the desired length of the spring structure 184. In that way, the linked aspect or side of the spring structure has a fixed length, but can change its curvature. If the bending moment caused the spring structure 184 to curve, there would generally be little resistance other than the relatively low flexural rigidity of the coil spring, until the coil portions on the aspect opposite the linked aspect came in contact with each other. Then a compressive force would prevent further substantial bending of the spring structure unless either the links or their respective wire portions fail in tension or shear, the lower-aspect wire segments fail in compression, or the entire spring buckles. In accordance with one aspect of the present invention, the design and material choice would be made such that any failure modes would be highly unlikely under expected loading or curvature. The links might be kept in position by a retaining feature which is secured appropriately to the link structures on the side of the coil. Alternatively, they might be allowed to move freely on the coil structure.

In the still further alternative embodiment, a fabric sheath, such as that described above with respect to FIGS. 13A, 13B, 14A, and 14B might be utilized with the structure illustrated in FIG. 15. The sheath in combination with the links 188 might be utilized to further limit curvature of the structure illustrated in FIG. 15.

Figure 16A:
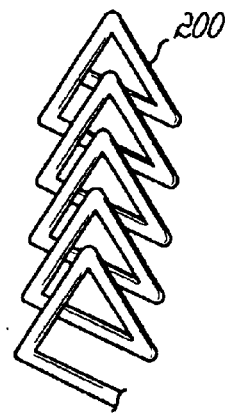
FIGS. 16A, B, C, D, E are partial perspective views of spring elements used in embodiments of the invention.
Figure 16B:
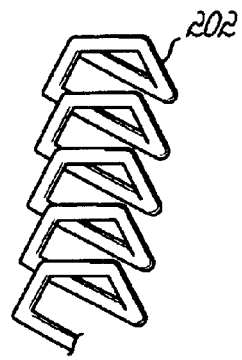
Figure 16C:
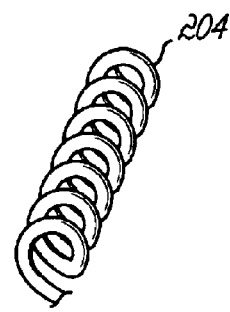
Figure 16D:
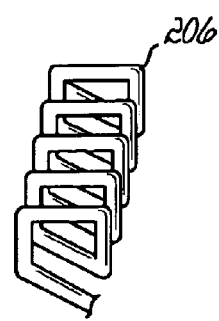
Figure 16E:
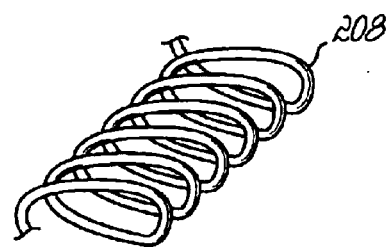

FIGS. 16A–16E illustrate various embodiments of a spring structure which might be utilized as described herein as a curvature limiting element. That is, these figures illustrate various different turn or coil shapes which might be utilized rather than simply circular coil shapes and turns of a standard helical coil. For example, the coils of spring structure 200, FIG. 16A, are generally triangular, while the coils of spring structure 202 are generally trapezoidal. Spring structure 204 has round coils and spring structures 206, 208 have coils which are rectangular with rounded corners and rectangular with rounded ends, respectively. It will be understood by a person of ordinary skill in the art that other spring structures might also be utilized.

While the present invention has been illustrated by the description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details representative apparatus and method, and illustrative examples shown and described. Accordingly, departures may be made from such details without departure from the spirit or scope of applicant's general inventive concept.

What is claimed is:

1. An actuation system for assisting the operation of a natural heart, the actuation system comprising:

an actuator element configured for being positioned proximate a portion of a heart wall and operable for acting on the heart wall portion to effect a change in the shape of the heart;

a shape-limiting element configured for being positioned proximate the heart wall, the shape-limiting element operable for flexing to assume a predetermined curvature when the heart wall is acted upon by the actuator element and maintaining the predetermined curvature to control the shape of the heart;

the shape-limiting element including a spring structure which is configured to flex;

a sheath interfacing with a portion of the spring structure, the sheath having limited deformability and configured to limit flexing of the spring structure to define said predetermined curvature.

2. The actuation system of claim 1 further comprising a framework for interfacing with the natural heart, the framework including an element configured for being anchored to tissue of the heart and the actuator element adapted to be coupled to the framework.

3. The actuation system of claim 1 wherein the shape-limiting element is coupled to the actuator element.

4. The actuation system of claim 2 wherein the shape-limiting element is coupled to the actuator element.

5. The actuation system of claim 1 wherein the shape-limiting element comprises:

a plurality of discrete links positioned to form a band, the links hingedly coupled together to hinge with respect to each other for varying the shape of the band;

at least two adjacent links being shaped to interfere with each other, when the adjacent links are hinged in a direction for a predetermined distance, to limit hinging and to maintain a predetermined curvature of the band.

6. The actuation system of claim 5 wherein the adjacent links include projections extending outwardly from a longitudinal axis of the band, the projections configured for interfering with each other.

7. The actuation system of claim 5 wherein said adjacent links are shaped to interfere with each other when hinged in both one direction and another direction.

8. The actuation system of claim 7 wherein the adjacent links are further configured to maintain one predetermined curvature when hinged in the one direction and to maintain a different predetermined curvature when hinged in the another direction.

9. The actuation system of claim 1 wherein the shape-limiting element comprises:

a plurality of discrete links positioned to form a band, the links hingedly coupled together to hinge with respect to each other for varying the shape of the band;

a tether spanning between at least two links, the tether having limited extensibility to limit hinging when the links are hinged in a direction for a predetermined distance to thereby maintain a predetermined curvature of the band.

10. The actuation system of claim 1 wherein the shape-limiting element comprises:

an elongated, flexible belt;

a plurality of projections extending outwardly from a longitudinal axis of the belt, the protrusions configured for interfering with each other, when the belt is flexed in a direction for a predetermined distance, to limit flexing and to maintain a predetermined curvature of the belt.

11. The actuation system of claim 1 wherein the shape-limiting element comprises:

an elongated, flexible belt, a tether fixed to the belt in at least two positions spaced along a longitudinal axis of the belt, the tether having limited extensibility to limit flexing of the belt when the belt is flexed in a direction for a predetermined distance to thereby maintain a predetermined curvature of the belt.

12. The actuation system of claim 1 wherein the shape-limiting element comprises:

a plurality of discrete links positioned to form a band, the links hingedly coupled together to hinge with respect to each other for varying the shape of the band;

a rigid stop element spanning between at least two links, the stop element configured to engage the links and limit hinging, when the links are hinged in a direction for a predetermined distance, to thereby maintain a predetermined curvature of the band.

13. The actuation system of claim 12 further comprising a rigid stop element spanning the links on opposite sides thereof and limiting hinging in both one direction and another direction.

14. The actuation system of claim 13 wherein the stop elements on the opposite sides of the links are further configured to maintain one predetermined curvature when the links are hinged in the one direction and to maintain a different predetermined curvature when the links are hinged in the another direction.

15. The actuation system of claim 13 wherein the stop elements on the opposite sides are coupled together between the links.

16. The actuation system of claim 15 wherein the stop elements are coupled together to form a generally unitary structure.

17. The actuation system of claim 1 wherein the shape-limiting element comprises:

a plurality of discrete links positioned to form a band, the links hingedly coupled together to hinge with respect to each other for varying the shape of the band;

a tubular stop element surrounding portions of at least two links and generally coaxial with a longitudinal axis of the band, the stop element configured to engage the links and limit hinging, when the adjacent links are hinged in a direction for a predetermined distance, to thereby maintain a predetermined curvature of the band.

18. The actuation system of claim 1 wherein the sheath encases a portion of the spring structure.

19. The actuation system of claim 1 wherein the spring structure is formed of a shape memory material.

20. A shape-limiting element for use with a heart wall actuation system to control the shape of an actuated heart, the element comprising:

a spring structure which is configured to flex;

a sheath having limited deformity and configured for interfacing with a portion of the spring structure, the sheath configured to limit flexing of the spring structure to define a predetermined curvature when the heart wall is acted upon by the heart wall actuation system.

21. The shape-limiting element of claim 20 wherein the sheath encases a portion of the spring structure.

22. The shape-limiting element of claim 20 wherein the spring structure is formed of at least one of stainless steel, titanium, and a shape memory material.

23. The shape-limiting element of claim 20 wherein the spring structure includes a plurality of turns, the curvature-limiting element including at least one link configured to couple with turns of the spring structure to limit the separation of the turns when the spring structure is flexed.

24. A method for assisting the operation of a natural heart, the method comprising:

positioning an actuator element proximate to the heart and operating the actuator element to act on a heart wall portion to effect a change in the shape of the heart;

positioning, proximate to the heart, a flexible spring structure and a sheath having limited deformability, which interfaces with a portion of the spring structure;

when the actuator element is operated to act on the heart wall portion, allowing the spring structure to flex to a predetermined curvature, limited by the sheath, and maintaining that predetermined curvature to control the shape of the actuated heart.

25. The method of claim 24 wherein the shape-limiting element comprises a plurality of discrete links positioned to form a band, the links hingedly coupled together to hinge with respect to each other for varying the shape of the band, the method further comprising limiting the hinging of links of the band to maintain a predetermined curvature of the band.

26. The method of claim 25 further comprising limiting the hinging of the links with projections on at least two links wherein the projections interfere with each other when the links are hinged.

27. The method of claim 25 further comprising limiting the hinging of the links with at least one tether spanning between at least two links and having limited extensibility.

28. The method of claim 24 wherein the shape-limiting element comprises an elongated, flexible belt, the method further comprising limiting the flexing of the belt to maintain a predetermined curvature of the belt.

29. The method of claim 28 further comprising limiting the flexing of the belt a at least tether fixed to the belt in at least two spaced positions along the belt, the tether having limited extensibility.

30. The method of claim 25 further comprising limiting the hinging of the links with at least one rigid stop element spanning between at least two links, the stop element configured to engage the links and limit hinging.

31. The method of claim 25 further comprising limiting the hinging of the links with at least one tubular stop element surrounding portions of at least two links, the stop element configured to engage the links and limit hinging.

32. The method of claim 24 wherein the shape-limiting element comprises a spring structure including a plurality of turns and at least one link configured to couple with turns of the spring structure to limit the separation of the turns when the spring structure is flexed.

* * * * *

UNITED STATES PATENT AND TRADEMARK OFFICE
CERTIFICATE OF CORRECTION

PATENT NO. : 6,988,982 B2
APPLICATION NO. : 10/223271
DATED : January 24, 2006
INVENTOR(S) : Melvin et al.

It is certified that error appears in the above-identified patent and that said Letters Patent is hereby corrected as shown below:

Column 1, line 18, reads "...circulatory system, and particularly, the proper operation of..." and should read --circulatory system, and particularly the proper operation of ... --.

Column 4, line 67, reads "...be hingedly coupled with the discreet links of the band." and should read -- ... be hingedly coupled with the discrete links of the band. --.

Column 6, line 9 reads "...system of one embodiment, is utilized with an actuator..." and should read -- ...system of one embodiment is utilized with an actuator... --.

Column 6, line 42 reads "...configuration and function of the heart is known to those..." and should read -- ... configuration and function of the heart are known to those ... --.

Column 8, line 8 reads "...of the heart 10 (See FIG. 1). The actuation system 72 has a..." and should read -- ...of the heart 10 (see FIG. 1). The actuation system 72 has a... --.

Column 10, line 31 reads "...of protections, or projection portions 108, which extend..." and should read -- ... of projections, or projection portions 108, which extend ... --.

Column 10, line 57 reads "...is illustrated, having multiple discreet links 112 which may..." and should read -- ... is illustrated, having multiple discrete links 112 which may...--.

Column 11, lines 26-28 read, "...band or belt, and fixed in intervals 146 to such surfaces. At the extent of flexion of the band or belt between tether fixation points. The corresponding segment of tether..." and should read -- ...band or belt, and fixed in intervals 146 to such surfaces. At the extent of flexion of the band or belt between tether fixation points, the corresponding segment of tether... --.

Column 11, line 29 reads, "...becomes taut and the bert or band flexion is limited to..." and should read -- ...becomes taut and the belt or band flexion is limited to... --.

Column 12, line 62 reads, "...and as illustrated and further discussed here and below, other..." and should read -- ...and as illustrated and further discussed herein below, other... --.

Column 13, line 47 reads, "The structure may be designed and build for specific minimum..." and should read -- The structure may be designed and built for specific minimum... --.

UNITED STATES PATENT AND TRADEMARK OFFICE
CERTIFICATE OF CORRECTION

PATENT NO. : 6,988,982 B2
APPLICATION NO. : 10/223271
DATED : January 24, 2006
INVENTOR(S) : Melvin et al.

It is certified that error appears in the above-identified patent and that said Letters Patent is hereby corrected as shown below:

Column 14, line 52 reads, "...is not the intention of the applicant to restrict or in any way..." and should read -- ...is not the intention of the applicants to restrict or in any way... --.

Column 14, line 56 reads,"...broader aspects is not limited to the specific details representative..." and should read -- ...broader aspects is not limited to the specific details, representative... --.

Column 14, line 60 reads, "...of applicant's general inventive concept." and should read -- ...of applicants' general inventive concept.--.

Column 18, CLAIM 29, line 6 reads, "...the flexing of the belt a at least tether fixed to the belt in at..." and should read -- ... the flexing of the belt with at least one tether fixed to the belt in at...--.

Signed and Sealed this

Twenty-first Day of August, 2007

JON W. DUDAS
*Director of the United States Patent and Trademark Office*